(12) United States Patent　(10) Patent No.: US 7,196,247 B2
Odell et al.　(45) Date of Patent: Mar. 27, 2007

(54) ROOT-SPECIFIC, STIMULANT INDUCIBLE PROMOTER AND ITS USE

(75) Inventors: Joan T. Odell, Unionville, PA (US); Xiaodan Yu, Chesterfield, MO (US); Xu Hu, Johnston, IA (US); Guihua Lu, Johnston, IA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 740 days.

(21) Appl. No.: 10/104,706

(22) Filed: Mar. 22, 2002

(65) Prior Publication Data

US 2003/0167507 A1　Sep. 4, 2003

Related U.S. Application Data

(60) Provisional application No. 60/311,461, filed on Aug. 10, 2001, provisional application No. 60/278,379, filed on Mar. 23, 2001.

(51) Int. Cl.
C12N 15/63　(2006.01)
C12N 15/82　(2006.01)
A01H 5/00　(2006.01)
A01H 5/06　(2006.01)

(52) U.S. Cl. .................. 800/312; 800/287; 800/298; 800/306; 800/314; 800/317.2; 800/317.3; 800/317.4; 800/320; 800/320.1; 800/320.2; 800/320.3; 800/322; 435/320.1; 536/23.1; 536/24.1

(58) Field of Classification Search ............... 536/23.1, 536/24.1; 800/278, 287, 298, 306, 312, 314, 800/320, 320.1, 320.2, 320.3, 317.2, 317.3, 800/317.4, 322

See application file for complete search history.

(56) References Cited

U.S. PATENT DOCUMENTS

| | | | |
|---|---|---|---|
| 4,683,195 A | 7/1987 | Mullis et al. |
| 4,800,159 A | 1/1989 | Mullis et al. |
| 4,945,050 A | 7/1990 | Sanford et al. |
| 5,107,065 A | 4/1992 | Shewmaker et al. |
| 5,231,020 A | 7/1993 | Jorgensen et al. |
| 5,459,252 A | 10/1995 | Conkling et al. |
| 5,750,399 A | 5/1998 | Dixon et al. |
| 5,846,784 A | 12/1998 | Hitz |
| 5,959,176 A | 9/1999 | Torikai et al. |

FOREIGN PATENT DOCUMENTS

| | | |
|---|---|---|
| WO | WO 94/02619 A1 | 2/1994 |
| WO | WO 98/16650 A1 | 4/1998 |
| WO | WO 98/59062 A1 | 12/1998 |
| WO | WO 00/29594 A1 | 5/2000 |

OTHER PUBLICATIONS

Keller B. et al. The Plant Cell, Oct. 1991, vol. 3, pp. 1051-1061.*
Yamamoto Y. et al., The Plant Cell, Apr. 1991, vol. 3, pp. 371-382.*
Yuri T. Yamamoto et. al., The Plant Cell, vol. 3:371-382, 1991, Characterization of Cis-Acting Sequences Regulating Root-Specific Gene Expression in Tobacco.
National Center for Biotechnology Information General Identifier No. 6979519, Feb. 16, 2000, Jung, W. et. al., Identification and Expression of Isoflavone Synthase, The Key Enzyme for Biosynthesis of Isoflavones in Legumes.
Woosuk Jung et. al., Nature Biotechnology, vol. 18:208-212, 2000, Identification and Expression of Isoflavone Synthase, The Key Enzyme for Biosynthesis of Isoflavones in Legumes.
Athel Cornish-Bowden, Nucleic Acids Research, vol. 13:3021-3030, 1985, Nomenclature Specified Bases in Nucleic Acid Sequences: Recommendations 1984.
Biochemical Journal, vol. 219:345-373, 1984, Nomenclature and Symobolism for Amino and Peptides.
Jack K. Okamuro et. al., Biochemistry of Plants, vol. 15:1-82, 1989, Regulation of Plant Gene Expression: General Principles.
Stephen F. Altschul et. al., J. Mol. Biol., vol. 215:403-410, 1990, Basic Local Alignment Search Tool.
Ivan L.W. Ingelbrecht et. al., The Plant Cell, vol. 1:671-680, 1989, Different 3' End Regions Strongly Influence the Level of Gene Expression in Plant Cells.
R. Deblaere et. al., Methods in Enzymology, vol. 153:277-292, 1987, Vectors for Cloning in Plant Cells.
T. M. Klein et. al., Nature, vol. 327:70-73, 1987, High-Velocity Microprojectiles for Delivering Nucleic Acids Into Living Cells.
A. Depicker et. al., Journal of Molecular and Applied Genetics, vol. 1:561-573, 1982, Nopaline Synthase: Transcript Mapping and DNA Sequence.
Nicole Bechtold et. al., CR Life Sciences, vol. 316:1194-1199, 1993, In Planta Agrobacterium Mediated Gene Transfer by Infiltration of Adult *Arabidopsis thaliana* Plants.
Richard R. Jefferson, Plant Molecular Biology Reporter, vol. 5:387-405, 1987, Assaying Chimeric Genes in Plants: The Gus Gene Fusion System.
Janice K. Sharp et. al., The Journal of Biological Chemistry, vol. 259:11312-11320, 1984. Purification and Partial Characterization of a B-Glucan Fragment That Elicits Phytoalexin Accumulation in Soybean.
S.C. Franca et. al., Genetics and Molecular Biology, vol. 24:243-250, 2001, Biosynthesis of Secondary Metabolites in Sugarcane.
Gert Forkmann et. al., Current Opinion in Biotechnology, vol. 12:155-160, 2001, Metabolic Engineering and Applications of Flavonoids.
Nancy H. Roosens et. al., Molecular Breeding, vol. 9:73-80, 2002, Overexpression of Ornithine-O-Aminotransferase Increases Proline Buisynthesis and Confers Osmotolerance in Transgenic Plants.
Woosuk Jung et. al., Nature Biotechnology, vol. 18:208-212, 2000, Identification and Expression of Isoflavone Synthase, The Key Enzume for Biosynthesis of Isoflavones in Legumes.
Senthil Subramanian et al., The promoters of two isoflavone synthase genes respond differentially to nodulatin and defense signals in transgenic soybean root, Plant Molecular Biology, vol. 54:823-839, 2004.

(Continued)

Primary Examiner—Russell P. Kallis

(57) ABSTRACT

This invention relates to an isolated isoflavone synthase 1 (IFS1) promoter nucleic acid fragment. The invention also relates to the construction of chimeric genes comprising all or a portion of the IFS1 promoter directing the expression of transgenes, in sense or antisense orientation.

14 Claims, 2 Drawing Sheets

OTHER PUBLICATIONS

Figure 1:
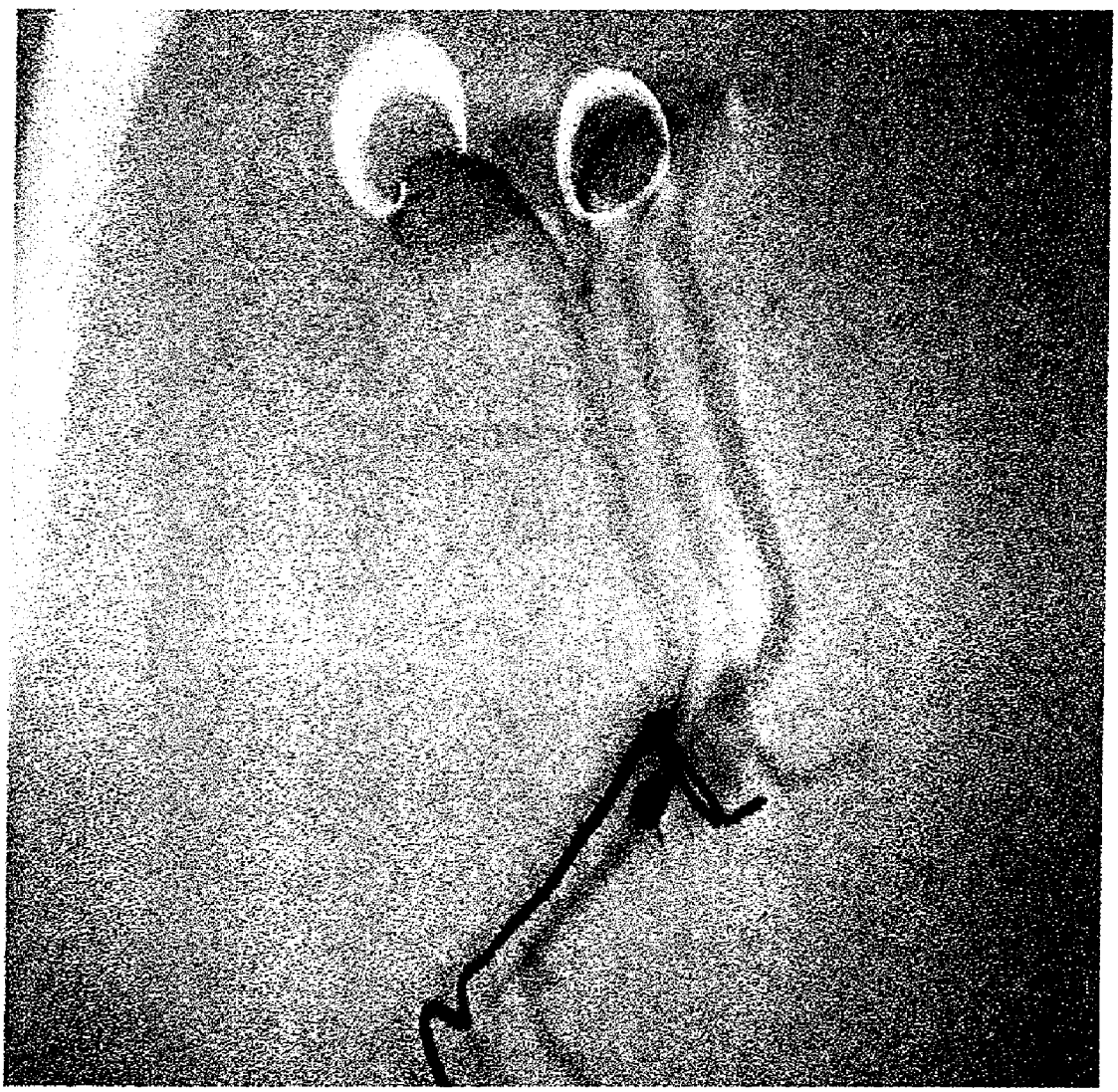

N.L. Paiva et al., Regulation of Isoflavonoid Metabolism in Alfalfa Plant Cell, Tissue and Organ Culture, 1984, pp. 213-220, vol. 38.
Embl, European Bioinformatics Institute, Accession No. AY530096, Dated Jun. 1, 2004, Glycine Max Isoflavone Synthase 1 Gene, Prometer Region, 5' UTR and Partical CDS.
Embl, European Bionformatics Institute, Accession No. AC007708, Dated Jun. 3, 1999. M. Zhan et al., Homo Sapiens Chromosome 22Q11 BAC Clone B563B9 In BCRL2-GGT Region.
Embl, European Bioinformatics Institute, Accession No. AL103436, Dated Jul. 26, 1999.

* cited by examiner

SEQUENCE LISTING

<160> NUMBER OF SEQ ID NOS: 17

<210> SEQ ID NO 1
<211> LENGTH: 1756
<212> TYPE: DNA
<213> ORGANISM: Glycine max

<400> SEQUENCE: 1

```
gtaattaacc tcactcaaac tcgggatcac agaaaccaac aacagttctt gcactgaggt      60
ttcacgatgt tgctggaact tgcacttggt ttgtttgtgt tagctttgtt tctgcacttg     120
cgtcccacac caagtgcaaa atcaaaagca cttcgccacc tcccaaaccc tccaagccca     180
aagcctcgtc ttcccttcat tggccaccctt cacctcttaa aagataaact tctccactat    240
gcactcatcg atctctccaa aaagcatggc cccttattct ctctctcctt cggctccatg     300
```

```
ccaaccgtcg ttgcctccac ccctgagttg ttcaagctct tcctccaaac ccacgaggca    360
acttccttca acacaaggtt ccaaacctct gccataagac gcctcactta cgacaactct    420
gtggccatgg ttccattcgg accttactgg aagttcgtga ggaagctcat catgaacgac    480
cttctcaacg ccaccaccgt caacaagctc aggcctttga ggacccaaca gatccgcaag    540
ttccttaggg ttatggccca agcgcagag gcccagaagc cccttgacgt caccgaggag    600
cttctcaaat ggaccaacag caccatctcc atgatgatgc tcggcgaggc tgaggagatc    660
agagacatcg ctcgcgaggt tcttaagatc ttcggcgaat acagcctcac tgacttcatc    720
tggcctttga agtatctcaa ggttggaaag tatgagaaga ggattgatga catcttgaac    780
aagttcgacc ctgtcgttga aagggtcatc aagaagcgcc gtgagatcgt cagaaggaga    840
aagaacggag aagttgttga gggcgaggcc agcggcgtct tcctcgacac tttgcttgaa    900
ttcgctgagg acgagaccat ggagatcaaa attaccaagg agcaaatcaa gggccttgtt    960
gtcgactttt tctctgcagg gacagattcc acagcggtgg caacagagtg ggcattggca   1020
gagctcatca acaatcccag ggtgttgcaa aaggctcgtg aggaggtcta cagtgttgtg   1080
ggcaaagata gactcgttga cgaagttgac actcaaaacc ttccttacat tagggccatt   1140
gtgaaggaga cattccgaat gcacccacca ctcccagtgg tcaaaagaaa gtgcacagaa   1200
gagtgtgaga ttaatgggta tgtgatccca gagggagcat tggttctttt caatgtttgg   1260
caagtaggaa gggaccccaa atactgggac agaccatcag aattccgtcc cgagaggttc   1320
ttagaaactg gtgctgaagg ggaagcaggg cctcttgatc ttaggggcca gcatttccaa   1380
ctcctcccat ttgggtctgg gaggagaatg tgccctggtg tcaatttggc tacttcagga   1440
atggcaacac ttcttgcatc tcttatccaa tgctttgacc tgcaagtgct gggccctcaa   1500
ggacaaatat tgaaggtga tgatgccaaa gttagcatgg aagagagagc tggcctcaca   1560
gttccaaggg cacatagtct cgtttgtgtt ccacttgcaa ggatcggcgt tgcatctaaa   1620
ctccttcctt aattaagata atcatcatat acaatagtag tgtcttgcca tcgcagttgc   1680
tttttatgta ttcataatca tcatttcaat aaggtgtgac tggtacttaa tcaagtaatt   1740
aaggttacat acatgc                                                   1756

<210> SEQ ID NO 2
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 2
ggtttgggag gtggcgaagt gvyyyyygatt tg                                  32

<210> SEQ ID NO 3
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 3
ctgttgttgg tttctgtgat cccgagtttg agtg                                 34

<210> SEQ ID NO 4
<211> LENGTH: 22
<212> TYPE: DNA
```

<213> ORGANISM: Artificial Sequence
<220> FEATURE:
<223> OTHER INFORMATION: Oligonucleotide Primer

<400> SEQUENCE: 4
gtaatacgac tcactatagg gc                                      22

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 5
actatagggc acgcgtggt                                          19

<210> SEQ ID NO 6
<211> LENGTH: 1231
<212> TYPE: DNA
<213> ORGANISM: Glycine max

<400> SEQUENCE: 6
atcaatactt aattttaaaa aatgcacctt gccgcaatcg tgatggatat ttaaatttct      60
tcttcacaaa atgccaagag aaatgcttgt taaaggtcgt actagttcag atacaaaata    120
caacttgccc agatgccctc gacttactcc aggcacaaca tttttttttta aaccggagta    180 tctttcagta aagaatcaag attatttaat ctctggaaat attaatatct tttaatattt    240
tggatgaaaa taattttatt taacttttaa ttgaatttta gattagttaa gatttttttc    300
ttgatatatt gaaagattaa gaaaaaatac tttatttaca tgtataagct taagattaaa    360
accctaatta tatataagat agaattatct gttaactatt atattatacc atatcagttg    420
tcacaacatg tgtttctggg gttattgcct cttgagttca attgcaactt gttaagcaaa    480
tcggccggct taagacctaa gcaacacaag caagggcttt aggttttcaa aaaaagggtt    540 ccaattttttt ttaatattaa tatatctcaa aaaaattatt ggaaaattat atttgaaaat    600 aagtttttaat taaaaatatt ataactaacc gttaatcttt ttattggtat tataaataat    660
aatcaatgag caacaattct tcaccgacat catatctttg gttttaaaaa ataataatt     720 ttaataaatt atttgatgaa taaataaaag attttattct taaatttatt ttaaatctct    780
ttgcgtcctt gaaagtccca tgatacagga tgagatattt gactatttga ctagaaacgt    840
agtaggtgat atatggacat ttcctggttt attttatatt cttaaaaaat aacaattcaa    900
tcgaatgtag ttgccaaatt ttaataaata ataaaaaga agcattcatc gaattcttcg    960
tcttttatga gtgtaaaaca aaacattgaa ttaggaacaa ttattatcac gttacttaaa   1020
ataaaatata ctaaaccgt tgaatgaaat cttcatattt gataagtgta ggtagaccca   1080
caacacaaac attgaataga ataaatttcc ccgtacagtg tcgtccacta tgtggctata   1140
aaatggaagc attgaaggtt gtttcctcag gccaagatct tggatagtaa ttaacctcac   1200
tcaaactcgg gatcacagaa accaacaaca g                                  1231

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 7

```
gagggcatct gggcaagttg tattttgtat ctg                              33

<210> SEQ ID NO 8
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 8
aaatatccat cacgattgcg gcaaggtgc                                  29

<210> SEQ ID NO 9
<211> LENGTH: 1338
<212> TYPE: DNA
<213> ORGANISM: Glycine max

<400> SEQUENCE: 9
actacgcttt gaaggagcac gtggatgttc aaagttgaac acacgcacca atttagttga    60
tcgaggtttt aactttctat agaaaagtat aggaaaagtg ttgatggtgg ttactttaga   120
tcttttatat cttttacaaa aactatgagg aattattttt aataataaaa ataatatttt   180
atctaacata taataatatt aaaaatgagt tttttaaaaa atttaaaatt tcttattatt   240
ataataaaat tatatataaa tttcttatgt gagaataaaa aaaataatgt aagaaattca   300
ctttaaaaaa ttcgattaaa gatgctgcta ttactttggt agagcagcag gctcctgaac   360
tcactggctg tctgtcttga ccatattatt aaattattat tattattatt attattatta   420
ttattattat tattattatt attattatta ttattatata caaaaaatca atgatagtgg   480
tgtatttatg aaattaatgt aagatggagg gtaggtatgg ggctttcccc atctacctcg   540
cttcacccct gtttgcaata gaaatagcat gtagacttca tcatttggat aatttaaaat   600
tcttcctact attttttatt tattaaaaaa gaaatcatac ttaagaaatt actatatgaa   660
atactttatc agctacggat aaaaataagc taataaaatt cgtatgtaat agagaattaa   720
ttgactttgc ttgggtgtca atacagttaa aatgtcaaga tctaatgtga tacttttata   780
tcaatgttta ttaaaaaaaa aagttaccaa taaattcatc ctcgtaagat tattttttaat   840 ctttgcattc acttaaaata tttatataaa aaaattgaaa cattattaca aagatattaa   900
ataagattta attttctctc tcatgtatcc tccttcaaga ataacagcgg atattcaatt   960
aaattaatca ttttatcgca taatattagt atactaataa tacagtaata gttaaattta  1020
ttaagtacat ctatataaaa acattttaca tgaattaaac cacttatatt gttttttatac  1080 aaagggaaa tgcatttgcc attgggcaac tctcaaaata aacttggcca gtccacacca  1140
attatcacta tcaagtgtga gtttcgaatc agccccacta aaattatttt aagtgtgaaa  1200
gttgtcaaat aacgtgtaat gactgaataa taaaataata aataaatgtg taatgacatt  1260
gactgatcag taataagtta gtggatatca atacttaatt ttaaaaaatg caccttgccg  1320
caatcgtgat ggatattt                                              1338

<210> SEQ ID NO 10
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 10
```

```
gcaacatcgt gaaacctcag tgcaagaac                                      29
```

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 11

```
gctttgaagg agcacgtgga tgttc                                          25
```

<210> SEQ ID NO 12
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 12

```
caccatggtg aaacctcagt gcaagaact                                      29
```

<210> SEQ ID NO 13
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 13

```
tataggaaaa gtgttgatgg tggttac                                        27
```

<210> SEQ ID NO 14
<211> LENGTH: 2682
<212> TYPE: DNA
<213> ORGANISM: Glycine max

<400> SEQUENCE: 14

```
actacgcttt gaaggagcac gtggatgttc aaagttgaac acacgcacca atttagttga      60
tcgaggtttt aactttctat agaaaagtat aggaaaagtg ttgatggtgg ttactttaga     120
tcttttatat cttttacaaa aactatgagg aattattttt aataataaaa ataatatttt     180
atctaacata taataatatt aaaaatgagt ttttaaaaa atttaaaatt tcttattatt      240
ataataaaat tatatataaa tttcttatgt gagaataaaa aaaataatgt aagaaattca     300
ctttaaaaaa ttcgattaaa gatgctgcta ttactttggt agagcagcag gctcctgaac     360
tcactggctg tctgtcttga ccatattatt aaattattat tattattatt attattatta     420
ttattattat tattattatt attattatta ttattatata caaaaaatca atgatagtgg     480
tgtatttatg aaattaatgt aagatggagg gtaggtatgg ggctttcccc atctacctcg     540
cttcacccct gtttgcaata gaaatagcat gtagacttca tcatttggat aatttaaaat     600
tcttcctact atttttttatt tattaaaaaa gaaatcatac ttaagaaatt actatatgaa     660
atactttatc agctacggat aaaaataagc taataaaatt cgtatgtaat agagaattaa     720
ttgactttgc ttgggtgtca atacagttaa aatgtcaaga tctaatgtga tacttttata     780
tcaatgttta ttaaaaaaaa aagttaccaa taaattcatc ctcgtaagat tattttttaat     840
ctttgcattc acttaaaata tttatataaa aaaattgaaa cattattaca aagatattaa     900
ataagattta atttttctctc tcatgtatcc tccttcaaga ataacagcgg atattcaatt     960
aaattaatca ttttatcgca taatattagt atactaataa tacagtaata gttaaattta    1020
```

```
ttaagtacat ctatataaaa acattttaca tgaattaaac cacttatatt gtttttatac    1080
aaaggggaaa tgcatttgcc attgggcaac tctcaaaata aacttggcca gtccacacca    1140
attatcacta tcaagtgtga gtttcgaatc agccccacta aaattatttt aagtgtgaaa    1200
gttgtcaaat aacgtgtaat gactgaataa taaataaata aataaatgtg taatgacatt    1260
gactgatcag taataagtta gtggatatca atacttaatt ttaaaaaatg caccttgccg    1320
caatcgtgat ggatatttaa atttcttctt cacaaaatgc caagagaaat gcttgttaaa    1380
ggtcgtacta gttcagatac aaaatacaac ttgcccagat gccctcgact tactccaggc    1440
acaacatttt tttttaaacc ggagtatctt tcagtaaaga atcaagatta tttaatctct    1500
ggaaatatta atatctttta atattttgga tgaaaataat tttatttaac ttttaattga    1560
attttagatt agttaagatt ttttttcttga tatattgaaa gattaagaaa aaatacttta    1620
tttacatgta taagcttaag attaaaaccc taattatata aagatagaa ttatctgtta     1680 actattatat tataccatat cagttgtcac aacatgtgtt tctggggtta ttgcctcttg    1740
agttcaattg caacttgtta agcaaatcgg ccggcttaag acctaagcaa cacaagcaag    1800
ggctttaggt tttcaaaaaa agggttccaa ttttttttaa tattaatata tctcaaaaaa    1860
attattggaa aattatattt gaaaataagt tttaattaaa aatattataa ctaaccgtta    1920
atctttttat tggtattata aataataatc aatgagcaac aattcttcac cgacatcata    1980
tctttggttt taaaaaaata ataatttaa taaattattt gatgaataaa taaaagattt     2040
tattcttaaa tttatttaa atctctttgc gtccttgaaa agtccatgat acaggatgag     2100
atatttgact atttgactag aaacgtagta ggtgatatat ggacatttcc tggtttattt    2160
tatattctta aaaataaca attcaatcga atgtagttgc caaattttaa taaataaata    2220 aaagaagca ttcatcgaat tcttcgtctt ttatgagtgt aaaacaaaac attgaattag     2280
gaacaattat tatcacgtta cttaaaataa aatatactaa aaccgttgaa tgaaatcttc    2340
atatttgata agtgtaggta gacccacaac acaaacattg aatagaataa atttccccgt    2400
acagtgtcgt ccactatgtg gctataaaat ggaagcattg aaggttgttt cctcaggcca    2460
agatcttgga tagtaattaa cctcactcaa actcgggatc acagaaacca acaacagttc    2520
ttgcactgag gtttcacgat gttgctggat gttgctggaa cttgcacttg gtttgtttgt    2580
gttagctttg tttctgcact tgcgtcccac accaagtgca aaatcaaaag cacttcgcca    2640
cctcccaaac cctccaagcc caaagcctcg tcttcccttc at    2682
```

<210> SEQ ID NO 15  
<211> LENGTH: 23  
<212> TYPE: DNA  
<213> ORGANISM: Artificial Sequence  
<220> FEATURE:  
<223> OTHER INFORMATION: PCR primer

<400> SEQUENCE: 15
ctcactcaaa ctcgggatca cag    23

<210> SEQ ID NO 16  
<211> LENGTH: 22  
<212> TYPE: DNA  
<213> ORGANISM: Artificial Sequence  
<220> FEATURE:  
<223> OTHER INFORMATION: PCR primer

<400> SEQUENCE: 16

|   |   |
|---|---|
| atccgcatca cgcagttcaa cg | 22 |

<210> SEQ ID NO 17
<211> LENGTH: 2538
<212> TYPE: DNA
<213> ORGANISM: Glycine max

<400> SEQUENCE: 17

|   |   |
|---|---|
| actacgcttt gaaggagcac gtggatgttc aaagttgaac acacgcacca atttagttga | 60 |
| tcgaggtttt aactttctat agaaaagtat aggaaaagtg ttgatggtgg ttactttaga | 120 |
| tcttttatat cttttacaaa aactatgagg aattattttt aataataaaa aataatattt | 180 |
| atctaacata taataatatt aaaaatgagt ttttttaaaaa atttaaaatt tcttattatt | 240 |
| ataataaaat tatatataaa tttcttatgt gagaataaaa aaaataatgt aagaaattca | 300 |
| ctttaaaaaa ttcgattaaa gatgctgcta ttactttggt agagcagcag gctcctgaac | 360 |
| tcactggctg tctgtcttga ccatattatt aaattattat tattattatt attattatta | 420 |
| ttattattat tattattatt attattatta ttattatata caaaaaatca atgatagtgg | 480 |
| tgtatttatg aaattaatgt aagatggagg gtaggtatgg ggctttcccc atctacctcg | 540 |
| cttcacccct gtttgcaata gaaatagcat gtagacttca tcatttggat aatttaaaat | 600 |
| tcttcctact attttttatt tattaaaaaa gaaatcatac ttagaaaatt actatatgaa | 660 |
| atactttatc agctacggat aaaaataagc taataaaatt cgtatgtaat agagaattaa | 720 |
| ttgactttgc ttgggtgtca atacagttaa aatgtcaaga tctaatgtga tacttttata | 780 |
| tcaatgttta ttaaaaaaaa aagttaccaa taaattcatc ctcgtaagat tattttttaat | 840 |
| ctttgcattc acttaaaata tttatataaa aaaattgaaa cattattaca aagatattaa | 900 |
| ataagattta attttctctc tcatgtatcc tccttcaaga ataacagcgg atattcaatt | 960 |
| aaattaatca ttttatcgca taatattagt atactaataa tacagtaata gttaaattta | 1020 |
| ttaagtacat ctatataaaa acattttaca tgaattaaac cacttatatt gtttttatac | 1080 |
| aaagggggaaa tgcatttgcc attgggcaac tctcaaaata aacttggcca gtccacacca | 1140 |
| attatcacta tcaagtgtga gtttcgaatc agccccacta aaattatttt aagtgtgaaa | 1200 |
| gttgtcaaat aacgtgtaat gactgaataa taaataaata aataaatgtg taatgacatt | 1260 |
| gactgatcag taataagtta gtggatatca atacttaatt ttaaaaaatg cacctttgccg | 1320 |
| caatcgtgat ggatatttaa atttcttctt cacaaaatgc caagagaaat gcttgttaaa | 1380 |
| ggtcgtacta gttcagatac aaaatacaac ttgcccagat gccctcgact tactccaggc | 1440 |
| acaacatttt tttttaaacc ggagtatctt tcagtaaaga atcaagatta tttaatctct | 1500 |
| ggaaatatta atatctttta atattttgga tgaaataat tttatttaac ttttaattga | 1560 |
| attttagatt agttaagatt tttttcttga tatattgaaa gattaagaaa aaatacttta | 1620 |
| tttacatgta taagcttaag attaaaaccc taattatata taagatagaa ttatctgtta | 1680 |
| actattatat tataccatat cagttgtcac aacatgtgtt tctggggtta ttgcctcttg | 1740 |
| agttcaattg caacttgtta agcaaatcgg ccggcttaag acctaagcaa cacaagcaag | 1800 |
| ggctttaggt tttcaaaaaa agggttccaa ttttttttaa tattaatata tctcaaaaaa | 1860 |
| attattggaa aattatattt gaaataagt tttaattaaa aatattataa ctaaccgtta | 1920 |
| atcttttttat tggtattata aataataatc aatgagcaac aattcttcac cgacatcata | 1980 |
| tctttggttt taaaaaaata ataattttaa taaattattt gatgaataaa taaaagattt | 2040 |
| tattcttaaa tttattttaa atctctttgc gtccttgaaa agtccatgat acaggatgag | 2100 |

```
atatttgact atttgactag aaacgtagta ggtgatatat ggacatttcc tggtttattt    2160
tatattctta aaaaataaca attcaatcga atgtagttgc caaattttaa taaataaata    2220
aaaagaagca ttcatcgaat tcttcgtctt ttatgagtgt aaaacaaaac attgaattag    2280
gaacaattat tatcacgtta cttaaaataa aatatactaa aaccgttgaa tgaaatcttc    2340
atatttgata agtgtaggta gacccacaac acaaacattg aatagaataa atttccccgt    2400
acagtgtcgt ccactatgtg gctataaaat ggaagcattg aaggttgttt cctcaggcca    2460
agatcttgga tagtaattaa cctcactcaa actcgggatc acagaaacca acaacagttc    2520
ttgcactgag gtttcacg                                                 2538
```

ROOT-SPECIFIC, STIMULANT INDUCIBLE PROMOTER AND ITS USE

RELATED APPLICATIONS

Priority is hereby claimed to U.S. provisional application No. 60/311,461, filed Aug. 10, 2001 and U.S. provisional application No. 60/278,279, filed Mar. 23, 2001, which are incorporated herein by reference in their entirety for all purposes as if included herein.

FIELD OF THE INVENTION

This invention is in the field of plant molecular biology. It refers to a plant promoter, more specifically, this invention pertains to nucleic acid fragments containing an isoflavone synthase 1 (IFS1) promoter and subfragments thereof and their use in directing transcription of transgenes in plants.

BACKGROUND OF THE INVENTION

The introduction of genes into plants has resulted in the development of plants having new and useful phenotypes such as pathogen resistance, higher levels of healthier types of oils, novel production of healthful components such as beta-carotene synthesis in rice, etc. An introduced gene is generally a chimeric gene composed of the coding region that confers the desired trait and regulatory sequences. One regulatory sequence is the promoter, which is located 5' to the coding region. This sequence is involved in regulating the pattern of expression of a coding region 3' thereof. The promoter sequence binds RNA polymerase complex as well as one or more transcription factors that are involved in producing the RNA transcript of the coding region.

The promoter region of a gene used in plant transformation is most often derived from a different source than is the coding region. It may be from a different gene of the same species of plant, from a different species of plant, from a plant virus, or it may be a composite of different natural and/or synthetic sequences. Properties of the promoter sequence generally determine the pattern of expression for the coding region that is operably linked to the promoter. Promoters with different characteristics of expression have been described. The promoter may confer constitutive expression as in the case of the widely-used cauliflower mosaic virus (CaMV) 35S promoter. The promoter may confer tissue-specific expression as in the case of the seed-specific phaseolin promoter. The promoter may confer a pattern for developmental changes in expression. The promoter may be induced by an applied chemical compound, or by an environmental condition applied to the plant.

The promoter that is used to regulate a particular coding region is determined by the desired expression pattern for that coding region, which itself is determined by the desired resulting phenotype in the plant. For example, herbicide resistance is desired throughout the plant so the 35S promoter is appropriate for expression of a herbicide-resistance gene. A seed-specific promoter is appropriate for changing the oil content of soybean seed. An endosperm-specific promoter is appropriate for changing the starch composition of corn seed. Control of expression of an introduced gene by the promoter is important because it is sometimes detrimental to have expression of an introduced gene in non-target tissues. For example, altering oil composition in cells throughout the plant would not be desirable.

In some cases it is desirable to have expression specifically in the roots of a plant. An example is for expression of coding regions that produce proteins for fighting pests that attack roots such as fungi (such as *Sclerotinia sclerotiorum*, among others), insects (such as corn rootworm, among others), and nematodes (such as soybean cyst nematodes and root knot nematodes, among others). Other examples might be for traits that would produce a better root system, with improved nutrient uptake or increased strength.

In the case of fighting plant pests, it is also desirable to have a promoter whose expression is induced by plant pathogens. Contact with the pathogen will induce expression of the promoter, such that a pathogen-fighting protein will be produced at a time when it will be effective in defending the plant. A pathogen-induced promoter may also be used to detect contact with a pathogen, for example by expression of a detectable marker, so that the need for application of pesticides can be assessed.

One reported root-specific and pathogen-induced promoter is the promoter from the alfalfa isoflavone reductase gene (U.S. Pat. No. 5,750,399). When transformed into tobacco plants, however, this promoter was also expressed in stem and floral tissues. It also showed much lower inducibility in tobacco cells than in alfalfa cells. Another root-specific gene promoter, the RB7 promoter sequence from tobacco (U.S. Pat. No. 5,459,252), has been shown to be able to direct expression of GUS in the root meristem and immature central cylinder regions (Yamamoto et al. (1991) *Plant Cell* 3:371–382). A carrot "root-specific" promoter has also been described (U.S. Pat. No. 5,959,176). Use of this promoter directs GUS to the vascular bundles, particularly in vascular bundles in root. However, the carrot "root-specific" promoter directs expression of GUS in the leaves of Arabidopsis plants.

Expression of foreign genes by tissue specific promoters in plants will allow the development of useful traits in plants. Therefore identification of a promoter that will regulate the expression of coding regions in a root-specific and pathogen-inducible manner is desirable.

SUMMARY OF THE INVENTION

The present invention concerns an isolated polynucleotide comprising a promoter wherein the promoter comprises a nucleotide sequence selected from substantially all of the nucleotide sequences set forth in SEQ ID NOs:6, 9, and 17, or portion thereof sufficient to induce root specific expression of a second nucleotide sequence; or a nucleic acid fragment that is sufficient to induce root specific expression of a second nucleotide sequence, and substantially similar to substantially all or a portion of the polynucleotide sequence set forth in SEQ ID NOs:6, 9, and 17.

In a second embodiment, the present invention relates to a chimeric gene comprising at least one polynucleotide operably linked to a promoter of the present invention. The polynucleotide may be in sense or antisense orientation with respect to the promoter. The chimeric gene may be introduced into a plant, a monocot or a dicot plant. The monocot plant may be, among others, corn, rice, wheat, barley and palm or the dicot plant may be, among others, *Arabidopsis*, soybean, oilseed *Brassica*, peanut, sunflower, safflower, cotton, tobacco, tomato, potato, and cocoa. It is preferable that the plant be soybean.

In a third embodiment this invention concerns grain or seed derived from a transgenic plant containing a chimeric gene comprising the promoter of the present invention, a fragment or subfragment thereof. The present invention also concerns an isolated nucleic acid fragment comprising an isoflavone synthase promoter.

In a fourth embodiment the present invention relates to a method of expressing all or a portion of an exogenous coding region in a plant cell comprising (a) transforming a plant cell with a chimeric gene comprising the promoter of the present invention; (b) regenerating stably transformed plants from the transformed plant cell; (c) selecting plants containing a transformed plant cell wherein expression of the chimeric gene results in production of a polypeptide not present in a plant not containing the chimeric gene. The present invention also concerns a method of altering the expression of at least one endogenous coding region in a plant cell, which comprises (a) transforming a plant cell with a chimeric gene comprising the promoter of the present invention; (b) regenerating stably transformed plants from the transformed plant cell; (c) selecting plants containing a transformed plant cell wherein expression of the polypeptide is altered compared to a plant cell not containing the chimeric gene. The plant having novel or altered expression of at least one polynucleotide sequence may be a monocot or a dicot. A monocot plant may be selected from corn, rice, wheat, barley and palm, and the dicot plant may be selected from *Arabidopsis*, soybean, oilseed *Brassica*, peanut, sunflower, safflower, cotton, tobacco, tomato, potato, and cocoa. It is preferable that the dicot plant be soybean.

In another embodiment the present invention relates to a method of expressing a nucleic acid fragment in the root of a plant by (a) transforming a plant cell with a chimeric gene containing the promoter of the present invention operably linked to a heterologous nucleic acid fragment; (b) regenerating stably transformed plants from the transformed plant cell; and (c) selecting plants containing a transformed plant cell wherein the heterologous nucleic acid fragment is expressed in the root of the transformed plant.

Yet another embodiment of the present invention concerns a method of altering the expression of the chimeric gene of the present invention in a first vegetative tissue and a second vegetative tissue comprising transforming a plant cell with the chimeric gene of the present invention; regenerating stably transformed plants from the transformed plant cell; exposing said transformed plant to a stimulant; and selecting plants containing a transformed plant cell wherein the chimeric gene is expressed in the first and second vegetative tissues of the transformed plant. The chimeric gene consists of a promoter of the present invention operably linked to a nucleic acid fragment. The stimulant includes and is not limited to, pathogen attack, fungal attack, fungal elicitor, or chemical elicitor.

BRIEF DESCRIPTION OF THE FIGURES AND SEQUENCE LISTINGS

The invention can be more fully understood from the following detailed description and the accompanying Figures and Sequence Listing which form a part of this application.

FIG. 1 depicts ten-day-old *Arabidopsis* transgenic plants transformed with pOY219. The plants were incubated in GUS Buffer for 2 hours in the dark at 28° C. and staining due to GUS activity visualized by light microscopy. To reveal any GUS activity in the leaf tissues the chlorophyll was removed by incubating the stained tissue in 75% ethanol. Accumulation of GUS activity was confined to the root tissue.

Figure 2:

FIG. 2 depicts ten-day-old *Arabidopsis* transgenic plants transformed with pOY219. The plants were incubated for 5 hours in prepared fungal elicitor prior to histochemical analysis for GUS. Plants were then incubated in GUS Buffer for 2 hours in the dark at 28° C. and staining due to GUS activity visualized by light microscopy. To reveal any GUS activity in the leaf tissues the chlorophyll was removed by incubating the stained tissue in 75% ethanol. Accumulation of GUS activity was detected in the root, stem and leaf tissues.

SEQ ID NO:1 is the nucleotide sequence of the isoflavone synthase gene (NCBI GI No. 6979519). The translation initiation ATG codon is located at nucleotides 67 through 69.

SEQ ID NO:2 is the nucleotide sequence of the oligonucleotide primer "Primer1" used in the first round of DNA walking to amplify the IFS1 promoter sequence. This primer corresponds to the complement of nucleotides 135 through 169 of the IFS1 gene sequence having NCBI GI No. 6979519.

SEQ ID NO:3 is the nucleotide sequence of the oligonucleotide primer "Primer2" used in the second round of DNA walking to amplify the IFS1 promoter sequence. This primer corresponds to the complement of nucleotides 10 through 45 of the IFS1 gene sequence having NCBI GI No. 6979519.

SEQ ID NO:4 is the nucleotide sequence of the oligonucleotide primer AP1 supplied with the Universal Genome Walker Kit and used in the first round of DNA walking to amplify the IFS1 promoter sequence.

SEQ ID NO:5 is the nucleotide sequence of the oligonucleotide primer AP2 supplied with the Universal Genome Walker Kit and used in the second round of DNA walking to amplify the IFS1 promoter sequence.

SEQ ID NO:6 is the nucleotide sequence of the insert in plasmid pOY151.

SEQ ID NO:7 is the nucleotide sequence of the oligonucleotide primer "Primer3" used in the second round of DNA walking to amplify the IFS1 promoter sequence. This primer corresponds to the complement of nucleotides 106 through 140 of the insert in clone pOY151.

SEQ ID NO:8 is the nucleotide sequence of the oligonucleotide primer "Primer4" used in the second round of DNA walking to amplify the IFS1 promoter sequence. This primer corresponds to the complement of nucleotides 22 through 52 of the insert in clone pOY151.

SEQ ID NO:9 is the nucleotide sequence of the cDNA insert in plasmid pOY166.

SEQ ID NO:10 is the nucleotide sequence of the oligonucleotide primer "Primer5" used to amplify the entire IFS1 promoter from the soybean genomic DNA. This primer corresponds to the complement of nucleotides 45 through 73 of the IFS1 gene sequence.

SEQ ID NO:11 is the nucleotide sequence of the oligonucleotide primer "Primer6" used to amplify the entire IFS1 promoter from the soybean genomic DNA. This primer corresponds to nucleotides 6 through 30 of PCR fragment insert in plasmid pOY166.

SEQ ID NO:12 is the nucleotide sequence of the oligonucleotide primer "Primer7" used to introduce an Nco I site at the translation start codon in the IFS1 gene. This primer corresponds to the complement of nucleotides 42 through 72 of the isoflavone synthase gene sequence and includes an Nco I site (CCATGG) at the initiation codon.

SEQ ID NO:13 is the nucleotide sequence of the oligonucleotide primer "Primer8" used to amplify the IFS1 promoter containing an Nco I site at the translation start codon. This primer corresponds to nucleotides 88 through 114 of the insert in plasmid pOY166.

SEQ ID NO:14 is the nucleotide sequence of the IFS1 promoter including the putative TATA box (nucleotides 2474 through 2480) and nucleotides 1 through 144 of the isoflavone synthase coding region (nucleotides 2539 through 2682).

SEQ ID NO:15 is the nucleotide sequence of the oligonucleotide primer "Primer9" used to identify the presence of the chimeric gene in transformed soybean embryos and plants.

SEQ ID NO:16 is the nucleotide sequence of the oligonucleotide primer "Primer10" used to identify the presence of the chimeric gene in transformed soybean embryos and plants.

SEQ ID NO:17 includes nucleotides 1–2538 of SEQ ID NO:14.

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The term "promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter, such as a cis-acting element, or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded and may, optionally, contain synthetic non-natural or altered nucleotide bases. A polynucleotide in the form of a polymer of DNA may be comprised of one or more segments of cDNA, genomic DNA, synthetic DNA, or mixtures thereof.

The terms "subfragment that is functionally equivalent" and "functionally equivalent subfragment" are used interchangeably herein. These terms refer to a portion or subsequence of a polynucleotide in which the ability to function as a root-specific promoter is retained. In addition, in response to a stimulant, the promoter or functionally equivalent portion thereof also expresses a chimeric gene in roots, stems and leaves. The size of the polynucleotide sequence that is required for specificity of the promoter activity varies between different characterized promoters. A promoter fragment is typically less than about 2.5 Kb. For example, the tobacco RB7 promoter has about 713 nucleotides, and a deletion of the RB7 promoter containing about 636 nucleotides is still capable of directing root-specific expression of GUS (Yamamoto et al. (1991) *Plant Cell* 3:371–382). The isoflavone reductase promoter has about 845 nucleotides of which nucleotides 1–765, 1–330, 330–845, 33–765 are capable of directing expression of GUS induced by development, elicitor, or infection (U.S. Pat. No. 5,750,399). Ely et al. have demonstrated that a fragment of about 4.2 Kb or a subfragment of about 1.9 Kb isolated from corn is capable of inducing expression of GUS in corn protoplasts isolated from different sources. They consider that the 4.2 Kb and the 1.9 Kb fragments were capable of inducing higher expression of GUS activity in transient assays in protoplasts derived from root, leaf, and endosperm tissue than were constitutive promoters such as the 35S and maize adh promoters (PCT publication No. WO 00/29594). Kriz et al. have isolated the gamma coixin promoter and have indicated that fragments of about 894 bp, about 412 bp, or about 222 bp are sufficient to direct expression of GUS in the endosperm of corn grains (PCT publication No. WO 99/58659). Also, Baszczynski et al. have shown that about 518 bp of the Gl1 F promoter are capable of inducing expression of GUS in transgenic canola plants (PCT publication No. WO 94/02619).

It is therefore envisioned that a polynucleotide fragment of shorter length than the entire 2.5 Kb IFS1 promoter may be sufficient to direct the expression of an operably linked coding region with substantially the same root-specific property. Indeed, it may be possible that a fragment of the promoter will induce root-specific expression that is not necessarily stress inducible, or may be stress-inducible but not root-specific and these fragments are also part of the invention. A shorter promoter fragment with functional identity may easily be obtained and identified through procedures standard in the art.

For example, the promoter fragment or subfragment can be used in the design of chimeric genes to produce a desired phenotype in a transformed plant. The chimeric gene will contain the fragment or subfragment of the root-specific promoter operably-linked to a DNA fragment. The DNA fragment may comprise a leader sequence, a coding region, and a termination signal. The DNA leader sequence may or may not be present and the coding region may be a fragment or a subfragment thereof. The coding region may or may not encode an active protein, but will result in a phenotype in a transformed plant. The coding region may be exogenous or endogenous to the plant where the chimeric gene is introduced. Chimeric genes can be designed for expression, overexpression, or co-suppression of a protein, in which case the promoter or promoter fragment will be located at the 5' terminus of the DNA fragment. In chimeric genes designed for antisense suppression the promoter or promoter fragment is located at the 3' terminus of the DNA fragment.

The term "isolated" polynucleotide refers to a polynucleotide that is substantially free from other nucleic acid sequences with which it is normally associated such as, and not limited to, other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "substantially similar" refers to nucleic acid fragments wherein changes in one or more nucleotide bases do not affect the ability of the nucleic acid fragment to mediate gene expression or produce a certain phenotype. This term also refers to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences and includes functional equivalents thereof. The terms "substantially similar" and "corresponding substantially" are used interchangeably herein.

A "substantial portion" of a nucleatide sequence comprises a nucleotide sequence that is sufficient to afford putative identification of the promoter that the nucleotide sequence comprises. Nucleotide sequences cart be evaluated either manually, by one skilled In the art, or using computer-based sequence comparison and identification tools that employ algorithms such as BLAST (Basic Local Alignment Search Tool; Altschul et al. (1993) *J. Mol Biol* 215:403–410; In general, a sequence of thirty or more contiguous nucleotides is necessary in order to putatively Identify a promoter nucleic acid sequence as homologous to a known promoter. The instant specification teaches nucleotide sequences comprising an IFS1 promoter. The skilled artisan, having the benefit of the sequences as reported herein, may now use all or a substantial portion of the disclosed sequences for purposes known to those skilled in this art. Accordingly, the instant Invention comprises the complete sequences as reported in the accompanying Sequence Usting, as well as substantial portions of those sequences as defined above.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene will comprise promoter sequences of the present invention directing the expression, in sense or anti-sense orientation, of proteins or polypeptides that are not normally associated with it. A chimeric gene may comprise regulatory sequences and coding sequences that are derived from different sources, or regulatory sequences and coding sequences derived from the same source, but arranged in a manner different than that found in nature. A promoter of the present invention may direct the expression of a coding region that is normally associated with it in a construct containing bases not normally found in the gene. "Endogenous gene" refers to a native gene in its natural location in the genome of an organism. "Exogenous" refers to a gene not normally found in the host organism, but that is introduced into the host organism by gene transfer. Exogenous genes include foreign genes, and can comprise native genes inserted into a non-native organism, or chimeric genes. A "transgene" is a gene that has been introduced into the genome by a transformation procedure. "Heterologous" is defined for purposes of the present invention as comprising different parts or elements, including those derived from elements not normally occurring in a designated part of the plant, and those from a separate genetic source or species. Heterologous includes endogenous and exogenous genes.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase 1.

"Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference).

The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA from a nucleic acid fragment using a promoter of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" or "altered expression" refers to the production of gene product(s) in transgenic organisms in amounts or proportions that differ from that of normal or non-transformed organisms. Accordingly, altered includes increase, enhance, amplify, multipy, and the like as well as decrease, reduce, lower, prevent, inhibit, stop, and the like. It also refers to the expression of a nucleic acid fragment in a tissue where it is not normally found, or at developmental stages where it is not expressed normally. Indeed, in accordance with the present invention, an endogenous gene may be expressed for the first time in response to a stimulant in the root, stem and leaf, for example.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

Examples of host cells which can be used to practice the invention include, but are not limited to, yeast, bacteria, and plants. The plants may be monocots or dicots. The monocot plants may include, but are not limited to corn, rice, wheat, barley and palm and the dicot plants may include, but are not limited to *Arabidopsis*, soybean, oilseed *Brassica*, peanut, sunflower, safflower, cotton, tobacco, tomato, potato, and cocoa.

The present invention concerns an isolated polynucleotide comprising a soybean isoflavone synthase promoter (IFS1) and its use to guide the expression of transgenes in plant roots. In response to stimulation, the promoter of the present invention results in expression of transgenes in the root and other parts of the plant.

In the present invention the promoter from the isoflavone synthase 1 gene (IFS1) of soybean has been isolated, sequenced, and modified for use in expressing an exogenous or endogenous coding region. For example, this promoter has been shown to confer root-specific expression to an operably-linked coding region both in germinating soybean seedlings and in stably transformed Arabidopsis plants. Upon induction by stress, i.e. a stimulant or stimulus, such as, and not limited to, fungal attack, a fungal elicitor, insect attack, nematode attack, or chemical elicitor, this promoter is capable of inducing expression of an exogenous or an endogenous coding region in vegetative tissue of a plant. For purposes of the present invention, vegetative tissues are defined to mean those tissues of the plant that are not involved in reproduction. Vegetative tissue includes and is not limited to root, stem, leaf, and the like. Attack for purposes of the present invention means to invade or occupy a plant. For example, in the case of nematodes and insects, attack includes and is not limited to biting a plant. In the case of fungi, attack includes and is not limited to coming into intimate contact with a plant. An elicitor, for purposes of the present invention, is something that causes the desired effect. In the case of a fungal elicitor, for example, it includes and is not limited to a chemical, compound, peptide, and the like, originating from a fungus following fractionation. In the case of a chemical elicitor, for example, it is a chemical or chemicals that cause the desired effect. Fungus includes and is not limited to *Penicillium* sp., *Sclerotinia* including and not limited to *Sclerotinia sclerotiorum*, and the like. A fungal elicitor in accordance with the present invention includes, inter alia, *Phytophthora sojae* cell wall extracts yeast extracts, *Rhizobia Nod* factors, and the like. Insects include, and are not limited to, corn root worm. Nematode includes, and is not limited to, soybean cyst nematode, sugarbeet nematode, corn knot nematode, and other plant parasitic nematodes. A chemical elicitor in accordance with the present invention includes, inter alia, salicylic acid, methyl jasmonic acid, glutathion, ethanol, heavy metals such as $Cu^{2+}$ and $Cd^{2+}$, and the like. In fact, the use of GUS as a reporter gene indicated that, under stimulus induction, this promoter directs expression of the reporter gene in the root, stem, and leaf tissue. This promoter can be used to regulate the expression of coding regions in cases where root-specific and/or stimulus-induced expression is required to produce the desired trait. Therefore the IFS1 promoter (IFS1/P) has utility for the expression, in a specific pattern, of introduced coding regions in plants to confer new traits that improve the plant's performance.

The disclosure of each reference set forth in this application is incorporated herein by reference in its entirety.

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions. Thus, various modifications of the invention in addition to those shown and described herein will be apparent to those skilled in the art from the foregoing description. Such modifications are also intended to fall within the scope of the appended claims.

EXAMPLES

Unless otherwise specified, all chemicals used in the following examples were obtained from Sigma Chemical Co. (St. Louis, Mo.) and all restriction endonucleases were obtained from GIBCO-BRL (Gaithersburg, Md.).

Example 1

Cloning and Identification of IFS1 Promoter Sequences

The IFS promoter was cloned using two rounds of DNA walking following the protocol provided with the Universal GenomeWalker Kit (Clontech Inc., Palo Alto, Calif.) with minor modifications. Two gene-specific primers required by the protocol were designed from the IFS1 gene sequence (Genebank Accession No. AF195798; SEQ ID NO:1) which contains 66 nucleotides 5' of the initiatior Methionine ATG codon. Primer1 (SEQ ID NO:2) corresponds to the complement of nucleotides 135–169 and Primer2 (SEQ ID NO:3) corresponds to the complement of nucleotides 10 through 45 of the IFS1 gene sequence.

```
                                                  (SEQ ID NO:2)
Primer1:  5'-GGTTTGGGAGGTGGCGAAGTGCTTTTGATTTTG-3'

(SEQ ID NO:3)
Primer2:  5'-CTGTTGTTGGTTTCTGTGATCCCGAGTTTGAGTG-3'
```

Genomic DNA from soybean (*Glycine max* cv. Wye) leaf tissue was extracted using the DNeasy Plant Maxi Kit (Qiagen Inc., Valencia, Calif.) following the manufacturer's protocol. The resulting DNA was digested with the seven endonuclease restriction enzymes, five provided with the "Universal Genome Walker Kit" (Dra I, Eco RV, Pvu II, Sca I, Stu I) and two additional blunt-ending enzymes (Hpa I and Sma I). Seven libraries (one per restriction enzyme digest) were constructed by ligating the digested fragments to the Genome Walker Adaptor from the kit.

Amplification was performed using DNA polymerase from the Expand High Fidelity PCR System Kit (Boehringer Mannheim, Roche Molecular Biochemicals, Indianapolis, Ind.) using a GeneAmp PCR System 9700 thermocycler (PE Applied Biosystems, Foster City, Calif.). The first round of PCR amplification used primer AP1 (SEQ ID NO:4; provided with the kit) and Primer1. Amplification conditions were: 94° C. for 3 min; 5 cycles of 94° C. for 20 sec and 70.5° C. for 3 min 30 sec; 35 cycles of 94° C. for 20 sec and 65.5° C. for 3 min 30 sec; followed by 66° C. for 7 min 20 Sec and holding at 4° C.

```
AP1:  5'-GTAATACGACTCACTATAGGGC-3'    (SEQ ID NO:4)

AP2:  5'-ACTATAGGGCACGCGTGGT-3'       (SEQ ID NO:5)
```

The resulting DNA was diluted 50 times with water and used for a second round of PCR amplification using primer AP2 (provided with the kit; SEQ ID NO:5) and Primer2. Amplification conditions were: 94° C. for 3 min; 5 cycles of 94° C. for 20 sec and 71° C. for 3 min 30 sec; 22 cycles of 94° C. for 20 sec and 66° C. for 3 min 30 sec; followed by 66° C. for 7 min 20 sec; and holding at 4° C.

A 1.2 Kb fragment amplified from the Eco RV library was cloned into vector pCR2.1-TOPO using the Topo TA Cloning Kit (Invitrogen Corp, Carlsbad, Calif.), following the manufacturer's protocol, to produce plasmid pOY151. The sequence of the cDNA insert in plasmid pOY151 is shown in SEQ ID NO:6, corresponds to nucleotides 1287 through 2517 of the IFS1 promoter sequence and contains a 45 nucleotide overlap with the reported IFS1 cDNA sequence. This fragment includes a putative TATA box located 116 nucleotides upstream of the IFS1 start codon.

To obtain a longer promoter fragment a second round of DNA walking was performed. For this purpose, two gene-specific primers were designed based on the sequence of the pOY151 PCR fragment insert with Primer3 (SEQ ID NO:7) corresponding to the complement of nucleotides 108 through 140 and Primer4 (SEQ ID NO:8) corresponding to the complement of nucleotides 24 through 52 of the insert in plasmid pOY151.

```
                                                  (SEQ ID NO:7)
Primer3:  5'-GAGGGCATCTGGGCAAGTTGTATTTTGTATCTG-3'

(SEQ ID NO:8)
Primer4:  5'-AAATATCCATCACGATTGCGGCAAGGTGC-3'
```

The seven libraries constructed above were amplified using the same amplification conditions as used in the first round of DNA walking and the following sets of primers. The first round of amplification used primers AP1 and Primer3 while the second round of amplification used primers AP2 and Primer4. From the resulting amplified products, a 1.3 Kb fragment from the Sca I library was isolated and cloned into the pCR2.1-TOPO vector resulting in plasmid pOY166. The sequence of the cDNA insert in plasmid pOY166 is shown in SEQ ID NO:9, corresponds to nucleotides 1 through 1338 of the IFS1 promoter sequence, and has a 51 nucleotide overlap with the cDNA insert in clone pOY151.

To amplify the entire IFS1 promoter from the soybean genomic DNA prepared above two primers were designed. Primer5 (SEQ ID NO:10) corresponds to the complement of nucleotides 43 to 73 of the IFS1 gene sequence and Primer6 (SEQ ID NO:11) corresponds to nucleotides 6 through 30 of the PCR fragment insert of plasmid pOY166.

```
                                              (SEQ ID NO:10)
    Primer5:  5'-GCAACATCGTGAAACCTCAGTGCAAGAAC-3'

(SEQ ID NO:11)
    Primer6:  5'-GCTTTGAAGGAGCACGTGGATGTTC-3'
```

The entire IFS1 promoter was amplified from the genomic DNA using Primer5 and Primer6 with the following amplification conditions: 94° C. for 4 min; 35 cycles of 94° C. for 30 sec, 52° C. for 30 sec, and 72° C. for 2 min 30 sec; followed by 72° C. 10 min; and holding at 4° C. The sequence of the IFS1 promoter is shown in SEQ ID NO:14.

To facilitate further cloning an Nco I restriction site was introduced in the resulting 2.5 kb DNA product at the translation start codon. To do this, the product from the last PCR amplification was diluted 100 fold with water and used as the template for another round of amplification using Primer7 and Primer8. The sequence for Primer7 (SEQ ID NO:12) corresponds to the complement of nucleotides 42 through 72 of the isoflavone synthase gene sequence but includes an Nco I site (CCATGG) at the initiation codon. Primer8 (SEQ ID NO:13) corresponds to nucleotides 88 through 114 of the insert in plasmid pOY166. This last primer was designed as a nested primer in order to increase PCR specificity. The amplification conditions used were the same as in the previous paragraph.

```
                                              (SEQ ID NO:12)
    Primer7:  5'-CACCATGGTGAAACCTCAGTGCAAGAACT-3'

(SEQ ID NO:13)
    Primer8:  5'-TATAGGAAAAGTGTTGATGGTGGTTAC-3'
```

Example 2

Transient Expression of GUS Under the Control of the IFS1 Promoter in Soybean Seedlings The activity of the IFS1 promoter was tested by its ability to direct the expression of the β-glucuronidase (GUS) reporter gene in transient assays in soybean seedlings. For this purpose, the 35S promoter in plasmid pMH40 was replaced for the newly isolated IFS1 promoter.

Plasmid pMH40 is derived from plasmid pGEM9z (Promega, Madison, Wis.) and contains a 1.3 Kb 35S promoter fragment from CaMV that extends 8 bp beyond (i.e., 3' of) the transcription start site coupled to a 60 bp untranslated leader DNA fragment derived from the chlorophyll a/b (cab) binding protein gene 22L. The cab leader is operably linked to the 5' end of the uidA coding region, which encodes GUS, and to an 800 bp DNA fragment containing the polyadenylation signal sequence region from the nopaline synthase gene. This plasmid is described in PCT publication No. WO 98/16650. A "pMH40 minus 35S promoter plasmid" was prepared by removing the 35S promoter sequence from plasmid pMH40 by digestion with Hind III, which cuts in the polylinker region immediately upstream of the 35S promoter, fill-in of the 5' overhangs using T4 DNA polymerase, and digestion with Nco I. The 2.5 kb IFS1 promoter fragment, containing an Nco I site at the IFS1 initiation codon and amplified above, was digested with Nco I and inserted into the "pMH40 minus 35S promoter plasmid" to prepare pOY175. This plasmid contains the 2.5 Kb promoter fragment to the Nco I site directing the expression of GUS with a Nos3' termination signal in a pUC19 vector background.

Soybean seeds (*Glycine max* cv. Wye) were germinated on a stack of wet paper towels in the dark for 4 days at 28° C. The seedlings, with an average length of 3 to 6 cm, were then transferred to Murashige and Skoog medium (1×MS salts (GIBCO BRL), 30 g/L sucrose, and 7 g/L Bacto-Agar (Becton Dickinson, Sparks, Md.)) for bombardment with DNA from plasmid pOY175 or plasmid pMH40. Bombardment was done following the transformation protocol of Klein T. M. et al. (*Nature* 1987 327:70–73). Briefly, the DNA was introduced using a DuPont Biolistic PDS 1000/He system for microprojectile bombardment. Gold particles (0.6 microns) were coated with 10 μg of DNA. Plates carrying the soybean seedlings were positioned approximately 3.5 inches away from the retaining screen and bombarded twice. Membrane rupture pressure was set at 1,100 psi and the chamber was evacuated to −28 inches of mercury.

Following the bombardment, the seedlings were incubated in dark at 28° C. for 16 hours to allow transient gene expression. For histochemical analysis the seedlings were submerged in GUS Buffer containing 1 mM 5-Bromo-4-chloro-3-indoxyl-beta-D-glucuronic acid cyclohexylammonium (X-Gluc, Biosynth AG, Switzerland) in 0.5% (v/v) N, N-Dimethyl Formamide, 10 mM Ethylene-diamine-tetraacetic acid (EDTA), 50 mM sodium phosphate buffer pH 7.0) for 2 hours in the dark at 28° C. Analysis was performed by light microscopy.

In plants expressing pOY175 the GUS activity was detected in both the lateral and tap roots, but was not found in the hypocotyl or cotyledons while in plants expressing pMH40, the control plasmid, GUS activity was detected in all four tissues.

Example 3

Transient Expression of GUS Under the Control of the IFS1 Promoter in Rice Roots The ability of the IFS1 promoter to transiently direct the expression of GUS in the roots of a monocot was tested by bombarding rice seedlings and roots with pOY175 (containing GUS under the control of the IFS1 promoter) followed by histochemical analysis.

Rice seed of the *Nipponbare* variety were germinated in the dark on wet filter paper and incubated for 6 days. Whole seedlings and roots detached from the seedlings were bombarded with gold particles coated with 3 μg of DNA from either pOY175 or pML63 following the protocol described in Example 2. Plasmid pML63 is derived from pMH40 (described above) by substitution of the 0.7 Kb fragment containing the Nos3' end for a 0.3 Kb fragment. Following bombardment the roots were incubated in the dark for 16 hours and then transferred to GUS buffer at 37° C. for 16 hours. No GUS activity was observed in the rice shoot bombarded with pOY175 DNA although GUS activity was observed in the control shoot (bombarded with pML63). Roots bombarded with pOY175 DNA showed localized spots of GUS activity while those bombarded with pML63 DNA showed widespread accumulation of GUS activity. These results show that the IFS1 promoter directs root specific expression of GUS in transient assays in rice roots.

Example 4

Expression of GUS Under the Control of the IFS1 Promoter in Transgenic Soybean The ability of the IFS1 promoter to direct the expression GUS in stably-transformed transgenic plants was analyzed. Somatic soybean embryo cultures were transformed, soybean plants were regenerated, and the presence of GUS activity visualized after submerging the samples in GUS buffer. The presence of active GUS was determined by the blue color produced.

Transformation of Somatic Soybean Embryo Cultures and Regeneration of Soybean Plants.

Soybean embryogenic suspension cultures were transformed with pOY175 in conjunction with pZBL100. Plasmid pZBL100 was prepared from pKS18HH (described in U.S. Pat. No. 5,846,784) by replacing the long Nos3' fragment in pKS18HH with a 285 bp fragment containing the polyadenylation signal sequence from the nopaline synthase gene (Depicker A. et al. (1982) *J. Mol. Appl. Genet.* 1:561–573). Transformations were performed by the method of particle gun bombardment, and transformants carrying the IFS1 promoter-GUS gene chimera were identified.

The following stock solutions and media were used for transformation and regeneration of soybean plants:

Stock solutions (per Liter):
MS Sulfate 100× Stock: 37.0 g $MgSO_4.7H_2O$, 1.69 g $MnSO_4.H_2O$, 0.86 g $ZnSO_4O.7H_2O$, 0.0025 g $CuSO_4.5H_2O$.
MS Halides 100× Stock: 44.0 g $CaCl_2.2H_2O$, 0.083 g KI, 0.00125 g $CoCl_2.6H_2O$, 17.0 g $KH_2PO_4$, 0.62 g $H_3BO_3$, 0.025 g $Na_2MoO_4.2H_2O$, 3.724 g $Na_2EDTA$, 2.784 g $FeSO_4.7H_2O$.
2,4-D: 10 mg/mL.
Vitamin B5 Stock: 10.0 g myo-inositol, 0.10 g nicotinic acid, 0.10 g pyridoxine HCl.

Media (per Liter)
SB55: 10 mL of each MS stock, 1 mL B5 Vitamin stock, 0.8 g $NH_4NO_3$, 3.033 g $KNO_3$, 1 mL 2,4-D stock, 0.667 g asparagine, pH 5.7.
SB103: 1 pk. Murashige & Skoog salt mixture, 60 g maltose, 2 g geirite, pH 5.7.
SB71-1: Gamborg's B5 salts (Gibco-BRL catalog No.21153–028), 1 ml B5 vitamin stock, 30 g sucrose, 750 mg $MgCl_2$, 2 g gelrite, pH 5.7.

Soybean embryonic suspension cultures were maintained in 35 mL liquid media (SB55) on a rotary shaker (150 rpm) at 28° C. with a mix of fluorescent and incandescent lights providing a 16 hour day/8 hour night cycle. Cultures were subcultured every 2 to 3 weeks by inoculating approximately 35 mg of tissue into 35 mL of fresh liquid media.

Soybean embryonic suspension cultures were transformed by the method of particle gun bombardment (see Klein et al. (1987) *Nature* 327:70–73) using a DuPont Biolistic PDS1000/He instrument.

Five μL of a 1:2 mixture of pOY175 at 1.0 μg/μl and pZBL100 at 0.5 μg/μl plasmid DNA were combined with 50 μL $CaCl_2$ (2.5 M) and 20 μL spermidine (0.1 M) and added to 50 μL of a 60 mg/mL 0.6 μm gold particle suspension. The mixture was agitated for 3 minutes, spun in a microfuge for 10 seconds, and the supernatant removed. The DNA-coated particles were then washed once with 400 μL of 100% ethanol and resuspended in 40 μL of anhydrous ethanol. The DNA/particle suspension was sonicated three times for 1 second each. Five μL of the DNA-coated gold particles was then loaded on each macro carrier disk.

Approximately 300 to 400 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded, and following bombardment, the tissue was divided in half, placed back into liquid media, and cultured as described above.

Eleven days after bombardment, the liquid media was exchanged with fresh SB55 containing 50 mg/mL hygromycin. The selective media was refreshed weekly. Seven weeks post-bombardment, green, transformed tissue was observed growing from untransformed, necrotic embryogenic clusters. Isolated green tissue was removed and inoculated into individual flasks to generate new, clonally-propagated, transformed embryogenic suspension cultures. Thus, each new line was treated as an independent transformation event. These suspensions can then be maintained as suspensions of embryos clustered in an immature developmental stage through subculture or can be regenerated into whole plants by maturation and germination of individual somatic embryos.

Transformed embryogenic clusters were removed from liquid culture and placed on solid agar media (SB103) containing no hormones or antibiotics. Embryos were cultured for eight weeks at 26° C. with mixed florescent and incandescent lights on a 16 hour day:8 hour night schedule. During this period, individual embryos were removed from the clusters and analyzed at various stages of embryo development. Selected lines were assayed by PCR for the presence of the chimeric gene, containing the IFS1 promoter and the GUS gene, using Primer9 (SEQ ID NO:15) and Primer10 (SEQ ID NO:16).

```
                                        SEQ ID NO:15
   Primer9:      5'-CTCACTCAAACTCGGGATCACAG-3'

SEQ ID NO:16
   Primer10:     5'-ATCCGCATCACGCAGTTCAACG-3'
```

These amplifications produce a 717 bp fragment in tissues containing the chimeric gene which is not present in tissues from wild type soybean embryos. The 717 bp fragment is indicative of the GUS coding region. Somatic embryos became suitable for germination after eight weeks and were then removed from the maturation medium and dried in empty petri dishes for 1 to 5 days. The dried embryos were then planted in SB71-1 medium where they were allowed to germinate under the same light and germination conditions described above. Germinated embryos were transferred to sterile soil and grown to maturity. GUS expression analysis.

Forty individual, 50-day-old, transgenic plants obtained from the above transformation experiment were assayed for the presence of GUS. Roots, leaves, leaf buds, stems, shoot meristem, floral meristem, flowers, pods, and developing immature seeds were assayed with GUS buffer as described above (mature seeds were not available at this time) and GUS expression was observed only in the root and root hairs.

Cross-sections (50 Mm) from the root of a transgenic plant showing GUS activity were obtained and observed under light microscopy. The blue staining was evenly distributed in all the root tissues, including the root hair, root epidermis, cortex, endodermis, and vascular parenchyma cells. These results suggest that GUS activity was evenly distributed in all root parts of transgenic plants containing the IFS1 promoter/GUS chimeric gene.

Example 5

Expression of GUS Under the IFS1 Promoter in Transgenic *Arabidopsis*

The ability of the soybean IFS1 promoter to direct the expression of GUS in transgenic *Arabidopsis* plants was tested. For this purpose, a plasmid was constructed containing the IFS1 promoter directing the expression of GUS in the *Agrobacterium tumefaciens* binary vector pZBL1 N. Plasmid pZBL1 N is derived from vector pZBL1. Vector pZBL1 is described in PCT publication No. WO 98/59062 and contains the origin of replication from pBR322, the bacterial nptII kanamycin resistance gene, the replication and stability regions of the *Pseudomonas aeruginosa* plasmid pVS1, T-DNA borders lacking nucleotides −320 to −116 of the OCS promoter, and a Nos/P-nptil-Ocs 3' gene (to serve as a kanamycin resistant plant selection marker). Plasmid pZBL1 has been deposited with the ATCC and bears Accession Number 209128. Plasmid pZBL1 N was prepared by digesting vector pZBL1 with Bam HI and Sal I and ligating a linker containing sequences encoding Bam HI, Xba I, Nco I, Sal I restriction enzyme sites. The polylinker sequence of plasmid pZBL1 N reads GGATCCTGTCTAGACCATGGT-TGTCGAC. Plasmid pZBL1 N was digested with Asp 718 and the 5' over-hang filled-in using T4 DNA polymerase. The promoter was removed from plasmid pZBL1 N by digestion with Sal I. Plasmid pOY175 was digested with Not I, the 5' over-hang filled-in using T4 DNA polymerase, and the resulting DNA was digested with Sal I to remove the IFS1 promoter/GUS fragment. This fragment was gel-isolated and inserted into the promoterless vector pZBL1N to create plasmid pOY219.

The pOY219 binary vector was transferred to *Agrobacterium tumefaciens* strain GV3101 using the freeze-thaw method (An et al. (1988) *Plant Molecular Biology Manual* A3: 1–19) and introduced into *Arabidopsis thaliana* via in planta vacuum infiltration following standard protocols (Bechtold et al. (1993) *CR Life Sciences* 316:1194–1199). Briefly, three-week-old *Arabidopsis thaliana* ectotype WS plants were submerged in 500 mL of *Agrobacterium* strain GV3101 harboring pOY219 suspended in basic MS media (GIBCO BRL) and vacuum was applied in 2 minute bursts repeatedly for 10 minutes. The infiltrated plants were allowed to set seeds for another three weeks. The harvested seeds were surface-sterilized, germinated and grown for three weeks on MS medium containing 75 mg/L kanamycin. Eight green healthy plants were recovered in the first round of screening and were transferred to soil and grown to maturity to harvest seeds. The R2 generation seeds were collected and germinated on kanamycin-containing medium.

For histochemical assays, both, 10-day-old *Arabidopsis* seedlings and 30-day-old *Arabidopsis* plants grown in soil were incubated in GUS Buffer for 2 hours in the dark at 28° C. and staining due to GUS activity visualized by light microscopy. In the seedlings, the GUS activity was localized to the roots. No activity was found in stems or cotyledons. All root tissues, including the root hairs and the root meristem, were stained. The root vascular tissue appeared to be stained more strongly than the cortex and epidermis tissues. In the adult plants only the root systems were stained including both of the tap roots and the lateral roots. There was no GUS activity detected in the remaining tissues including leaves, stems, shoot meristisms, inflorescences, flowers, siliques, and seeds. These results show that gene expression driven by the soybean IFS1 promoter in heterologous transgenic *Arabidopsis* plants was root-specific.

Example 6

Plant-Defense Induction of GUS Expression Under the IFS1 Promoter in Transgenic Arabidonsis Induction of IFS1 Promoter-Driven Expression by Non-virulent Fungal Challenge The ability of pathogen attack to induce IFS1 promoter driven expression in tissues other than the root was determined. *Arabidopsis* plants transformed with the plasmid expressing GUS under the control of the IFS1 promoter (pOY219) were treated with a non-virulent fungus *Penicillium* sp. and assayed for GUS expression. Upon fungal infection, GUS activity was detected in the transgenic roots, as described previously, and in the stems of fungal-treated transgenic *Arabidopsis* plants.

A fungal solution was prepared by resuspending a 5-day-old *Penicillium* sp. colony in water. Ten-day-old *Arabidopsis* seedlings transformed with pOY219 were submerged for 5 hours, at room temperature, in either water or fungal solution. For histochemical assays, the seedlings were incubated in GUS Buffer for 2 hours in the dark at 28° C. and staining due to GUS activity visualized by light microscopy. In water-treated controls GUS activity was confined to the root tissue, however, in the fungus-challenged tissue, GUS activity was also observed in the stem tissue, which had previously not shown GUS activity. These results indicate that IFS1 promoter-driven gene expression was induced upon fungal challenge. No GUS activity was detected when non-transformed seedlings were incubated in the fungal solution followed by submerging in GUS buffer indicating that the staining was not due to induction of the fungal p-glucuronidase.

Induction of IFS1 Promoter-Driven Expression by Virulent Fungal Challenge

The ability of pathogen attack to induce IFS1 promoter driven expression in root and stem tissues was further determined using a virulent fungal pathogen, *Sclerotinia sclerotiorum* (isolate 255M[7]). *Arabidopsis* plants transformed with the plasmid expressing GUS under the control of the IFS1 promoter (pOY219) were inoculated with a *Sclerotinia sclerotiorum* (isolate 255M[7]) and assayed for GUS expression. The stems of 30-day-old transgenic *Arabidopsis* plants were inoculated with a PDA plug (3 mm in diameter) with active growing mycelium. Three days later the GUS activity was detected in the transgenic roots and stem tissues using fluorimetric GUS assays (as described by Jefferson R. A. (1987) *Plant Mol. Biol. Rep.* 5:387–405). The GUS activity in the roots and stems of fungal-treated transgenic *Arabidopsis* plants was about 2 to 3-fold higher than that in the non-infected plants.

Induction of IFS1 Promoter-Driven Expression by Fungal Elicitor Preparation

Induction of expression directed by the IFS1 promoter in other tissues, besides the root, by prepared fungal elicitor was determined. Ten-day-old *Arabidopsis* transgenic plants transformed with pOY219 were incubated for 5 hours in prepared fungal elicitor prior to histochemical analysis for GUS. Besides expression in the roots, GUS activity was also observed in stem and leaf tissue.

Fungal-derived elicitors were prepared following the method of Sharp et al. using cell wall extract from the fungal pathogen *Phytophthora megasperma* sojae (Sharp, J. K. et al. (1984) *J. Biol. Chem.* 259:11312–11320). Ten-day-old transgenic *Arabidopsis* plants transformed with pOY219 were submerged in 0.1% (w/v) of acidified fungal elicitors in 10 mM $KH_2PO_4$, 10% (v/v) ethanol, and 10 μM glutathione. For histochemical analysis, after 5 hours in elicitor, the seedlings were submerged in GUS Buffer for 2 hours in the dark at 28° C. To reveal any GUS activity in the leaf tissues the chlorophyll was removed by incubating the stained tissue in 75% ethanol. As described previously the GUS activity was confined to the root tissue in transgenic plants incubated in water (FIG. 1), while in the elicitor-treated samples the GUS activity was observed in the roots as well as in the stem and leaf tissue (FIG. 2). These results indicate that fungal elicitor treatment induced gene expression directed by the IFS1 promoter in other tissues besides the root.

Induction of IFS1 Promoter-Driven Expression by Salicylic Acid

Salicylic acid (SA) is an important secondary messenger of plant systemic acquired response. Induction by SA of IFS1 promoter directed expression in other tissues besides the root was determined. *Arabidopsis* seedlings were incubated in different concentrations of SA for 4 hours followed by submerging in GUS buffer for histochemical assays. Besides the roots, GUS activity was also observed in the stem tissue and the staining was stronger depending on the concentration of SA in the incubating buffer.

Ten-day-old *Arabidopsis* transgenic seedlings transformed with plasmid pOY261 were submerged in either 200 μM or 600 μM SA. After incubation in SA for 4 hours at room temperature the seedlings were stained in GUS buffer for 2 hours in the dark at 28° C. GUS activity was detected in the roots of all seedlings and in the stem tissue of SA-treated seedlings with the staining appearing stronger in the seedlings incubated in 600 μM SA. These results suggest that gene expression under the control of the IFS1 promoter was induced by SA treatment and that this induction was dosage dependent.

Example 7

Isolation of Subfragments of the 2.5 Kb IFS1 Promoter and Their Characterization for Functional Equivalence Less than the 2.5 Kb of the IFS1 promoter are required to induce expression in a root-specific and/or inducible manner. To determine the fragments that conserve the properties, a series of constructs containing truncated IFS1 promoter linked to the sequences for GUS and the Nos3' end are constructed and tested in transient assays in soybean seedlings, in stably transformed soybean plants, and/or in stably transformed Arabidopsis plants.

A Sal I site located 3' to the Nos3' sequence used in conjunction with different restriction sites located within the 2.5 Kb IFS1 promoter fragment permits the isolation of the GUS-Nos3' gene operably linked to different lengths of the 2.5 Kb IFS1 promoter fragment. Digestion with Bgl II allows the isolation of a chimeric gene with 77 bp of the IFS1 promoter. Partial digestion with Eco RI allows the isolation of a chimeric gene with 301 bp of the IFS1 promoter. Partial digestion with Eco RI is necessary due to the presence of an Eco RI site at the 3' end of the GUS coding region. Digestion using Pac I allows the isolation of a chimeric gene with 641 bp of the IFS1 promoter. Digestion with Hind III allows the isolation of a chimeric gene with 904 bp of the IFS1 promoter. Using a Spe I site a chimeric gene with 1149 bp of the IFS1 promoter is prepared. Using a partial digestion with Bgl II a chimeric gene with 1778 bp of the IFS1 promoter is prepared. Each of these fragments is cloned into pBluescriptII (Stratagene, La Jolla, Calif. 92037), using matching polylinker sites, except Pac I which is filled in with T4 DNA polymerase and ligated to the blunt Sma I site. Additional promoter subfragments are prepared by using primers derived from the 2.5 Kb IFS1 promoter sequence in PCR reactions having pOY175 as template.

Each of the promoter truncation-GUS-Nos3' constructs is assayed as described in Examples 2 through 5. Promoter subfragments directing root-specific and/or stress-inducible expression of GUS are identified and considered to have functional equivalence to the 2.5 Kb IFS1 promoter.

Example 8

Expression of GUS Under the IFS1 Promoter in Transgenic Soybean Hairy Roots and Induction of GUS expression by Nematode Infection The ability of the IFS1 promoter to direct the expression of GUS in stably-transformed transgenic soybean hairy roots was analyzed, and the induction of GUS activity under IFS1 promoter by nematode infection was tested using these hairy roots.

The following stock solutions and media were used for transformation and regeneration of soybean roots:

Stock Solutions (per Liter):
B-5 Majors: 25.00 g $KNO_3$, 1.34 g $(NH_4)_2 SO_4$, 2.50 g $MgSO_4.7H_2O$, 1.50 g $CaCl_2.2H_2O$, 1.31 g $NaH_2PO_4$ (anhydrous).
B-5 Minors: 1.00 g $MnSO_4.H_2O$, 0.30 g $H_3BO_3$, 0.20 g $ZnSO_4.7H_2O$, 0.075 g Kl.
B-5 Vitamin B-5 Stock with Thiamine: 1 L Vitamin B-5 Stock, 1 g Thiamine HCl.
Iron Mix: 3.73 g. $Na_2EDTA$, 2.78 g $FeSO_4.7H2O$.

Media (per Liter):
Minimal A medium: 10.5 g $K_2HPO_4$, 4.5 g $KH_2PO_4$, 1.0 g $(NH_4)_2SO4$, 0.5 g $(Na)_2C_6H_5O_7.2H_2O$, 1 ml 1.0 M $MgSO_4.7H2O$ 10 ml 20% w/v sucrose, 15 g agar.
0 B-5 medium: 0.6 g MES [2-(N-Morpholino) ethanesulfonic acid (M5287, Sigma), 20 g sucrose, 10 ml B-5 minors, 100 ml B-5 majors, 10 ml B-5 Vitamin Stock with Thiamine, 10 ml Iron mix.
MXB medium: Murashige and Skoog Basal nutrient salts (M5524, Sigma), 10 ml Vitamin B-5 Stock with Thiamine, 30 g sucrose.
MXB medium with geirite: add 3 g gelrite to 1 L MXB medium, pH 5.7.
MXB medium with Daishiin agar: add 8 gbDaishiin agar to 1 L MXB medium, pH 6.5.

Generation of Soybean Transgenic Hairy Roots

*Agrobactrium rhizogenes* strain K599 was used for the soybean hairy root transformation and maintained on Minimal A media. Plasmid pOY219 DNA was introduced into *A. rhizogenes* strain K599 using the freeze-thaw method (Ha. S. B. In *Plant Molecular Manual* (1988) S. B. Gelvin, R. A. Schilperoort, and D. P. S. Verma, Eds. pp A3/1–A3/7).

Soybean seeds were surface-sterilized by setting in a bell jar with chlorine gas at room temperature for 12–16 hours.

The seeds were then aerated in a clean air hood for at least 30 min. Seeds were germinated and cultured in magenta boxes containing sterile potting soil having 10 to 15 ml of 25% Gamborg's B-5 Basal medium with minimal organics (G5893, Sigma) at 26° C. under a mix of fluorescent and incandescent lights providing a 16-hour day/8-hour night cycle. The hypocotyl of 6-days-old seedlings of non-transformed plants were inoculated with a freshly grown culture of A. rhizogenes previously transformed with pOY219. Hypocotyls just under the cotyledons were wounded 4 to 6 times in the epidermal cell layer with a 23-gauge needle containing the transformed A. rhizogenes. Inoculated plants were cultured under the same conditions used for seed germination.

Adventitious soybean roots, that developed after inoculation of the soybean hypocotyls with A. rhizogenes, were excised. Initially these putative transformed roots were cultured in liquid 0 B-5 medium with antibiotics [500 mg/L cefotaxime (Calbiochem-Novabiochem, La Jolla, Calif.) and 200 mg/L vancomycin (Spectrum Quality Products, Los Angeles, Calif.)] to cure the roots of any bacteria. Roots were transferred to fresh liquid medium every 2–3 days for a total of three times. After the third transfer, each root was moved to a plate of MXB medium with gelrite. To select for transformed roots, a root piece (1 to 2 cm) was placed in a 1.5 mL tube with GUS staining solution (0.05% X-Gluc in 100 mM sodium phosphate buffer, pH 7.0, containing 10 mM EDTA, 0.1% Triton, and 0.5 mM $K_4Fe(CN).6H_2O$), incubated for 2 to 4 hours at 27 to 29° C., and the roots watched closely for development of blue color indicative of GUS activity. Roots showing GUS activity and controls were cultured in MXB medium with gelrite in an incubator without light, set at 26 to 30° C. A 1–4 cm piece of root tip was excised and transferred to fresh medium every 2–4 weeks.

Soybean Cyst Nematode (SCN) Infection

Roots for SCN infection assay were transferred to 6-well plates containing MXB medium with Daishiin agar and inoculated 4–10 days later with second-stage SCN Heterodera glycines Ichinohe juveniles. Two to five root tips were placed in each well. Roots transformed with A. rhyzogenes containing pOY219 were in four of the six wells and the other two wells were used for roots transformed with A. rhizogenes not containing pOY219. These two controls were from an SCN-susceptible soybean line such as Pioneer 9204, referred to as an SCN-compatible control, and from an SCN-resistant soybean genotype such as Jack, referred to as an SCN-incompatible control. Roots were inoculated by placing 500 second stage SCN race 3 juveniles directly onto the roots in each well and incubating for 7 days at 26 to 28° C.

Histochemical Analysis of GUS Expression in SCN Feeding Sites

Root samples infected with SCN and control samples were fixed in 0.1% glutaraldehyde in 25 mM phosphate buffer pH 7.0 using a vacuum at 15 psi for 2 minutes. After washing in 25 mM phosphate buffer pH 7.0, root samples were immersed in GUS staining solution and infiltrated for 2 minutes at 15 psi. The samples were incubated for an additional 12 hours at 37° C. The nematodes were stained with acid fuchsin by boiling the root samples in 200 nM acid fuchsin in 147 mM acetic acid for 2 minutes. Root samples were examined under a dissecting microscope for SCN-hairy root interactions and GUS expression patterns. Four to six mm segments showing GUS activity and/or SCN infection were dissected for thin section, were fixed in 3% glutaraldehyde in 25 mM phosphate buffer for 2 hours, and washed three times in 25 mM phosphate buffer pH 7.0 for 30 minutes at room temperature. Root segments were dehydrated through an ethanol series of 30%, 50%, 70%, 95%, and three changes in 100%, 30 min per ethanol wash. A gradual buffer exchange was carried out to replace ethanol with Histoclear (100%), and then with paraffin at 60° C. Roots were sectioned (10 μm) with a Leica microtome and examined under light microscopy.

Strong GUS expression was observed in endodermal cells near SCN juveniles. This phenomena was not seen in uninfected roots. These results indicate that gene expression in the endodermal cells, under the control of the IFS1 promoter, was induced by nematode infection. Endodermal cells are the cell layers that lie outside the pericycle cell layers. Cyst nematodes induce and develop feeding sites in pericycle cells.

While not intending to be bound by any theory or theories of operation, the IFS1 promoter may be used to express anti-nematode protein factors or nematode resistance genes in "constitutive" and "inducible" expression manners. These expression patterns provide efficient control of the penetration, infection, and development of nematodes.

What is claimed is:

1. An isolated polynucleotide comprising a promoter having the nucleotide sequence of SEQ ID NO: 17 operably linked to a nucleotide fragment, wherein expression of said nucleotide fragment by the promoter is root specific.

2. A recombinant construct comprising the isolated polynucleotide of claim 1.

3. A plant comprising the recombinant construct of claim 2.

4. The plant of claim 3 wherein said plant is selected from the group consisting of a monocot and a dicot.

5. The plant of claim 3 wherein said plant is a monocot selected from the group consisting of corn, rice, wheat, barley and palm.

6. The plant of claim 3 wherein said plant is a dicot selected from the group consisting of Arabidopsis, soybean, oilseed Brassica, peanut, sunflower, safflower, cotton, tobacco, tomato, potato, and cocoa.

7. The plant of claim 6 wherein said plant is soybean.

8. Transgenic grain from the plant of claim 3 comprising the recombinant construct of claim 2.

9. A method of expressing a polypeptide in root cells comprising:
   (a) transforming a plant cell with the recombinant construct of claim 2, wherein the nucleotide fragment comprises an exogenous coding region coding for a polypeptide;
   (b) selecting for a transformed plant cell of (a); and
   (c) regenerating a stably transformed plant from the transformed plant cell of (b), wherein expression of the nucleotide fragment results in expression of the polypeptide in root cells.

10. The method of claim 9 wherein said plant is selected from the group consisting of a monocot and a dicot.

11. The method of claim 9 wherein the plant is a monocot selected from the group consisting of corn, rice, wheat, barley and palm.

12. The method of claim 9 wherein the plant is a dicot selected from the group consisting of Arabidopsis, soybean, oilseed Brassica, peanut, sunflower, safflower, cotton, tobacco, tomato, potato, and cocoa.

13. The method of claim 12 wherein the plant is soybean.

14. A method of expressing a nucleotide fragment in the root of a plant comprising:
   (a) transforming a plant cell with the recombinant construct of claim 2;
   (b) selecting for a transformed plant cell of (a); and
   (c) regenerating a stably transformed plant from the transformed plant cell of (b), wherein the nucleotide fragment is expressed in the root of the transformed plant.

* * * * *